United States Patent [19]

Messinger

[11] Patent Number: 5,148,811
[45] Date of Patent: * Sep. 22, 1992

[54] METHOD AND APPARATUS FOR SAMPLING BLOOD AND FOR MONITORING BLOOD PRESSURE

[75] Inventor: Phillip D. Messinger, Powell, Ohio

[73] Assignee: Medex, Inc., Hilliard, Ohio

[*] Notice: The portion of the term of this patent subsequent to Sep. 17, 2008 has been disclaimed.

[21] Appl. No.: 577,153

[22] Filed: Sep. 4, 1990

Related U.S. Application Data

[63] Continuation-in-part of Ser. No. 524,224, May 15, 1990, Pat. No. 5,048,537.

[51] Int. Cl.$^5$ .............................................. A61B 5/02
[52] U.S. Cl. ..................................... 128/673; 128/760; 604/52
[58] Field of Search ............... 128/760, 762, 768, 672, 128/673; 604/4, 51, 52, 53, 181, 187, 141, 142

[56] References Cited

U.S. PATENT DOCUMENTS

| | | |
|---|---|---|
| 986,263 | 3/1911 | Bevill . |
| 3,057,350 | 10/1962 | Cowley . |
| 3,157,201 | 11/1964 | Littmann . |
| 3,276,472 | 10/1966 | Jinkens et al. . |
| 3,340,869 | 9/1967 | Bane . |
| 3,898,988 | 8/1975 | Morgan . |
| 4,105,500 | 8/1978 | Libman et al. . |
| 4,114,617 | 9/1978 | Turner et al. . |
| 4,219,021 | 8/1980 | Fink . |
| 4,263,922 | 4/1981 | White . |
| 4,289,648 | 9/1981 | Hoskins et al. . |
| 4,300,572 | 11/1981 | Knighton ............................ 128/674 |
| 4,316,473 | 2/1982 | Beskin ................................. 128/763 |
| 4,341,224 | 7/1982 | Stevens ............................... 128/675 |
| 4,370,987 | 2/1983 | Bazell et al. ........................ 128/760 |
| 4,385,637 | 5/1983 | Akhavi ................................ 128/763 |
| 4,431,009 | 4/1984 | Marino, Jr. et al. ................ 128/673 |
| 4,447,235 | 5/1984 | Clarke ................................. 604/169 |
| 4,457,753 | 7/1984 | Pastrone ............................. 604/153 |
| 4,474,574 | 10/1984 | Wolfe et al. .......................... 604/85 |
| 4,533,348 | 8/1985 | Wolfe et al. .......................... 604/85 |
| 4,535,818 | 8/1985 | Duncan et al. ..................... 137/846 |
| 4,566,480 | 1/1986 | Parham ............................... 137/271 |
| 4,608,996 | 9/1986 | Brown ................................. 128/760 |
| 4,610,256 | 9/1986 | Wallace .............................. 128/675 |
| 4,673,386 | 6/1987 | Gordon ................................ 604/48 |
| 4,763,648 | 8/1988 | Wyatt .................................. 128/673 |
| 4,796,644 | 1/1989 | Polaschegg ........................ 128/760 |
| 4,830,013 | 5/1989 | Maxwell ............................. 128/637 |
| 4,865,583 | 9/1989 | Tu ........................................ 604/53 |
| 4,981,140 | 1/1991 | Wyatt .................................. 128/673 |
| 5,002,066 | 3/1991 | Simpson et al. .................... 128/760 |

FOREIGN PATENT DOCUMENTS

WO88/01846 3/1988 PCT Int'l Appl. .
2143803 2/1985 United Kingdom .

*Primary Examiner*—Max Hindenburg
*Assistant Examiner*—Guy V. Tucker
*Attorney, Agent, or Firm*—Wood, Herron & Evans

[57] ABSTRACT

A source of saline solution under pressure is connected through tubing to a catheter inserted in a patient's blood vessel. A waste collection bag is connected to the tubing through a stopcock which permits the selective connecting of the catheter to the waste collection bag or the bag of saline solution. The sampling site is in the tubing between the catheter and the stopcock. Normally, saline solution flows into the patient's blood vessel. When a sample is to be taken, the stopcock is shifted so that the pressure of the patient's blood forces blood into the tubing, driving saline into the waste collection bag. When blood has reached the sampling site, blood is extracted with a hypodermic syringe.

5 Claims, 2 Drawing Sheets

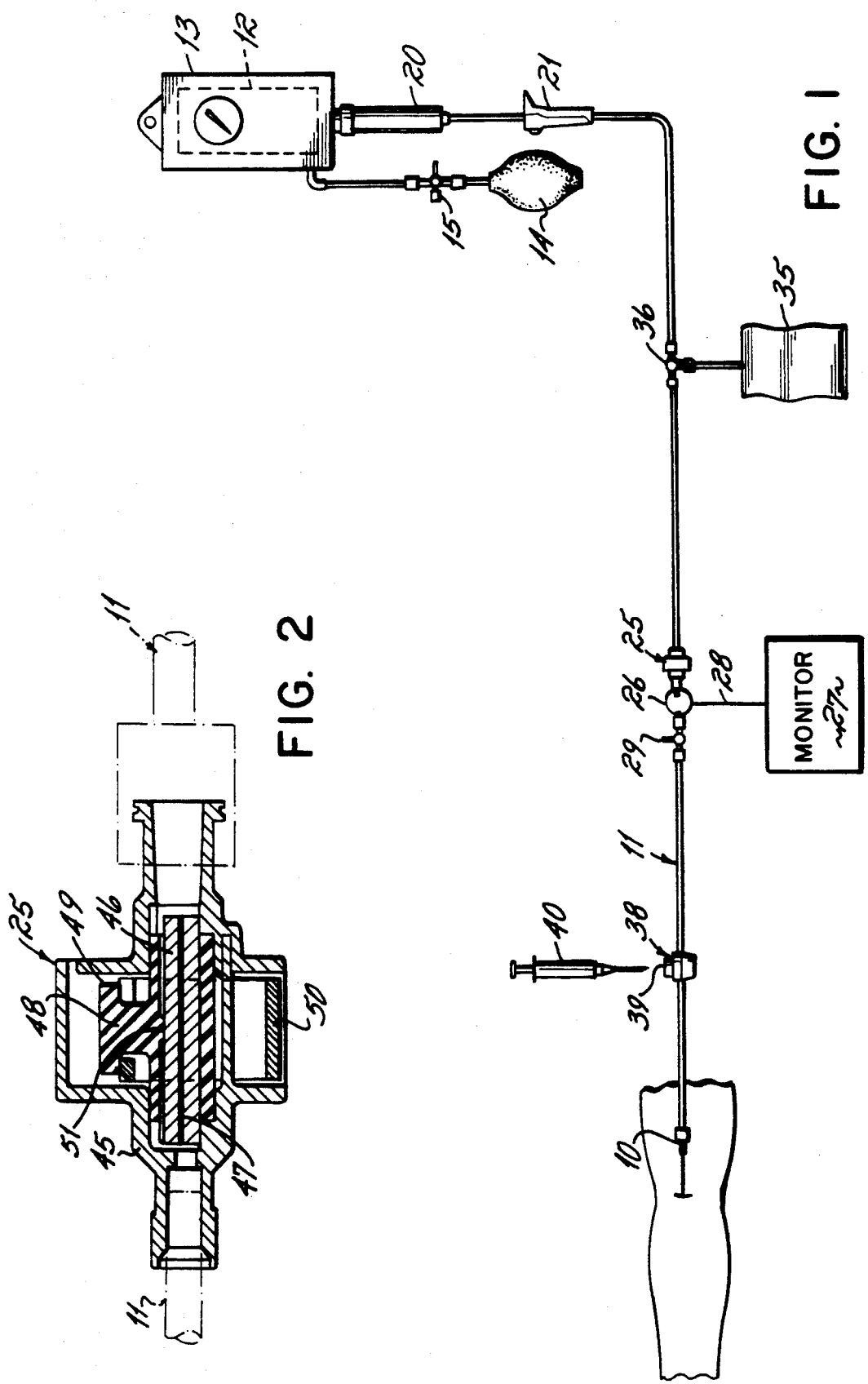

5,148,811

METHOD AND APPARATUS FOR SAMPLING BLOOD AND FOR MONITORING BLOOD PRESSURE

This is a continuation-in-part of U.S. application Ser. No. 07/524,224, filed May 15, 1990, now U.S. Pat. No. 5,048,537.

This invention relates to blood pressure monitoring apparatus, and particularly the invention relates to apparatus for removing samples of a patient's blood during a blood pressure monitoring procedure.

BACKGROUND OF THE INVENTION

Blood pressure monitoring apparatus is well known. It includes a catheter inserted into a patient's blood vessel, a tube connecting the catheter to a transducer, a supply of saline solution connected through the transducer to the catheter and a flush valve connected in the line to the catheter. The system through the catheter is filled with the saline solution, the saline solution forming a static column between the patient's blood vessel and the transducer whereby variations in blood pressure are communicated to the transducer so that the patient's blood pressure is monitored in real time. The flush valve has a capillary through which the saline solution flows, very slowly, to the patient. The slow dripping of the saline solution prevents any clotting of blood in the catheter which might introduce an error into the monitoring of the blood pressure. The flush valve contains a bypass by which a rapid flow of saline solution can be introduced into the system as needed.

It has been conventional to provide a site for withdrawing a blood sample. A stopcock is placed in series between the catheter and the transducer. The stopcock has a port that is normally closed by a solid plug (dead ender). The procedure for drawing a blood sample through the free port on the stopcock has required the following major steps: The stopcock is shifted to block flow of saline solution from the supply and open ports between the catheter and the plugged port. The dead ender plug is removed and carefully set aside to avoid contamination. A syringe is inserted in the opening created by the removal of the dead ender and about 3–5 cc mixture of blood and saline is withdrawn to remove the saline from the catheter and tube leading to the stopcock so that only whole blood is present at the free port of the stopcock. A heparinized syringe is inserted into the free stopcock port to withdraw about 1 or more cc of blood. The stopcock is shifted to open the free port to the saline supply and block the port to the catheter. The free port is flushed, using the flush valve, with saline and the dead ender is replaced. The stopcock is then shifted again to block the free port and connect the catheter to the saline supply. The flush valve then flushes the blood out of the tube and catheter, whereupon the system between the catheter and transducer is filled and ready for resumption of normal monitoring operation.

The foregoing procedure has obvious disadvantages. A number of manipulative steps are required to obtain the blood sample. A number of chances for contamination of the patient's blood are presented in the opening of the port to bring the blood to the stopcock for sampling. Blood usually drips from the sampling port. The exposure of attending people to the patient's blood is a matter of considerable concern because of the possibility of spreading AIDS, hepatitis and the like.

In copending application Ser. No. 07/288,568, filed Dec. 22, 1988, now U.S. Pat. No. 5,022,066 an improved sampling system is disclosed. There, a T-connection is connected to the tubing between the saline source and the catheter via a stopcock. The T-connection has an antiseptic syringe on one port and a sampling site on the other port. The antiseptic syringe is used to draw saline or a combination of saline and blood into the syringe until the liquid at the sampling site is pure blood. Thereafter, a hypodermic syringe is employed to withdraw blood from the sampling site. The antiseptic syringe thereafter returns the saline to the system.

BRIEF SUMMARY OF THE INVENTION

The objective of the present invention has been to provide an improved system for taking samples of blood and specifically a system that does not require any syringe to pull saline solution and blood to the sampling site.

The objective of the invention is achieved by the mounting of a flexible waste collection bag by means of a stopcock to the tubing between the pressurized saline bag and the catheter. A sampling site is mounted in the tubing between the catheter and the stopcock.

The bag of saline solution is normally pressurized to about 300 mmHg. The patient's internal cardiovascular system is pressurized normally at about 100 mmHg. The flexible collection bag in the beginning is at about 0 mmHg relative to atmospheric pressure and never exceeds a pressure of about 30 mmHg. By shifting the stopcock from normal operation wherein 300 mmHg is forcing saline solution into the patient's blood vessel, to sampling operation connecting the patient to the collection bag, the patient's cardiovascular system at 100 mmHg pumps blood towards the waste collection bag.

Thus, there is no need for the attendant to manipulate a syringe to withdraw saline in order to bring blood to a sampling site. Rather, the pressure in the patient's blood vessel pumps the saline into the waste collection bag until blood in the tubing reaches the sampling site.

The closed system of the present invention allows the attendant to perform the following operations:

a) Infuse needed fluids into patient.

b) Monitor patient's blood pressure.

c) Pump blood from the patient towards the waste collection bag to move blood to a sampling site.

d) Collect waste fluids in a separate collection bag.

e) Adjust the rate that blood enters or leaves the system.

f) Return unused blood to the patient.

All of the foregoing functions can be performed without any blood or fluids contacting the outside environment.

In any invasive system of the type described herein, it is important to prime the system free of air bubbles. There is an obvious difficulty in so priming the waste collection bag and connecting tubing. The importance of the matter is that, if there is residual air in the system, an air bubble could enter the patient's circulatory system with consequent hazards to the patient.

To address this potential problem, it is a feature of the invention to insulate any movement of air from the air waste collection bag to the main line between the source of saline solution and the catheter in the patient's blood vessel. In one embodiment of the invention, a one-way check valve, preferably in the form of a duck bill valve, is placed between the collection bag and the stopcock. In another form of the invention, an air elimination filter which permits the passage of fluid but prevents the passage of air is connected between the collection bag and the stopcock.

Another feature of the invention has been to provide alternate structures for extracting blood from a sampling site. In one form of the invention, a simple sampling site is provided, the sampling site presenting a port filled with a latex. That port is penetrated by the needle of a hypodermic syringe to withdraw blood when it has been brought to the sampling site in accordance with the invention. In the alternative form of the invention, the injection site is included as a port of a two-position (antishunt) stopcock. In one position of the stopcock, normal flow of saline between the source and the catheter is provided. In the other position of the stopcock, only flow between the third port of the stopcock and the catheter in the patient is permitted. The third port of the stopcock is preferably provided with a Luer fitting and the syringe utilized to withdraw blood from the sampling site has no needle, but rather has a mating Luer fitting permitting the syringe to be connected to the third port of the stopcock.

BRIEF DESCRIPTION OF THE DRAWINGS

The several features and objectives of the present invention will become more readily apparent from the following detailed description taken in conjunction with the accompanying drawings in which:

FIG. 1 is a diagrammatic view of the closed blood sampling system;

FIG. 2 is an enlarged cross-sectional view of a flush device employed in the system;

DETAILED DESCRIPTION OF THE DRAWINGS

Figure 3:
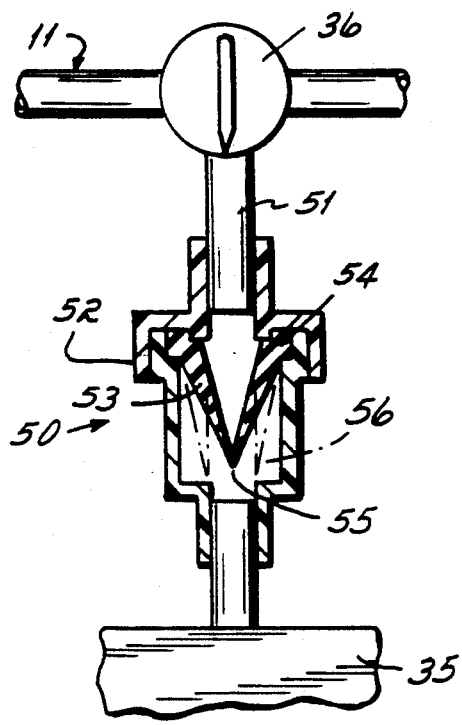
FIG. 3 is an enlarged cross-sectional view of one embodiment of the connection between the collection bag and stopcock.
Figure 4:
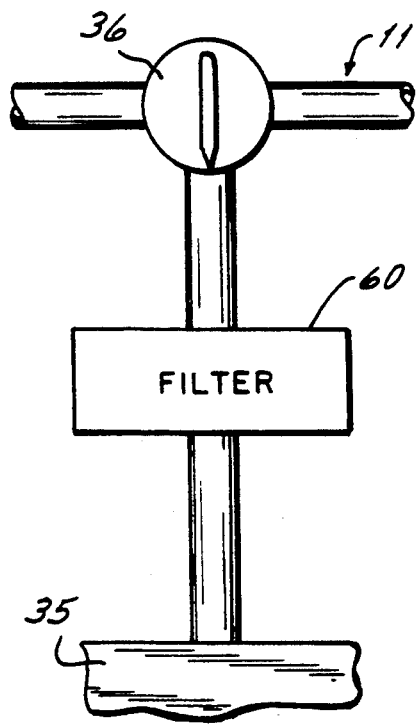
FIG. 4 is an enlarged cross-sectional view of another embodiment of the connection between the collection bag and the stopcock.

Referring to FIG. 1, there is disclosed a catheter 10 for insertion into a patient's blood vessel. The catheter 10 is connected by transparent tubing 11 to a bag 12 of saline solution. The bag 12 is wrapped in a pressure cuff 13 that can be inflated by an inflation squeeze bulb 14 through a stopcock 15. The pressure cuff 13 is of the type disclosed in U.S. Pat. No. 4,551,136, which disclosure is fully incorporated herein by reference. It wraps about a bag of saline solution 12 and is inflatable to pressurize the bag of saline solution, normally to a pressure of about 300 mmHg.

The bag 12 is connected to the transparent tubing 11 by a conventional drip chamber 20. A roller clamp 21 is mounted on the tubing adjacent the drip chamber 20 in order to selectively block the flow of saline from the bag toward the patient. The tubing contains a flush device 25 as depicted in FIG. 2 and will be described in greater detail below. Its function is to restrict flow of saline to the patient in the normal operation to approximately 3 cc of saline per hour. The flush device 25 has a parallel passage that permits flow to increase (adjustably) to approximately 120 cc per minute. A transducer 26 is mounted in the tubing between the flush device 25 and the catheter 10 and is electrically connected to a monitor 27 by a cable 28 for monitoring the patient's blood pressure. A transducer of the type disclosed in U.S. Pat. No. 4,920,972, fully incorporated herein by reference, can be employed. A three-way stopcock 29 is connected between the transducer 26 and the catheter 10 and is normally used for an initial connection of the system to atmospheric pressure to zero the monitor 27. Thereafter, it remains set to permit flow to the patient.

The system thus far described is, in general, a conventional system for providing the continuous monitoring of a patient's blood pressure. The invention consists of the connecting to that system of a waste collection bag 35 by means of a shunted stopcock 36. The shunted stopcock 36 has two positions. In one position, flow is permitted from the saline bag 12 to the catheter 10. In the other position, flow is permitted from the catheter 10 to the waste collection bag 35.

A blood sampling site 38 is connected between the transducer 26 and the catheter 10. The sampling site is a T-connection that is connected in series with the tubing 11 and has a port 39 that is filled with latex which can be penetrated by a hypodermic needle. A hypodermic syringe 40 is connected to the site when a blood sample is to be taken.

The flush device 25 may be of the type depicted in FIG. 2. It is connected in series with the tubing 11. It has a housing 45 in which is mounted a marine capillary tube 46 having a very small bore 47. The small bore permits a flow of about 3 cc per hour when the saline solution is pressurized to 300 mmHg. Surrounding the capillary tube is an elastic pull tube 48 having a flanged knob 49. A push button 50, connected to the knob 49, will, when pushed, stretch the elastic pull tube 48, pulling it away from the capillary tube by the flanged knob 49. The pull tube has a dam 51 which normally blocks flow of fluid around the capillary tube 46, thus forcing the fluid through the capillary tube 46. However, when the push button is depressed to create the flush condition, the fluid flows rapidly, up to 120 cc per minute around the capillary tube. That volume per minute can be controlled by the distance the push button 50 is depressed.

In the operation of the invention, the bag of saline 12 under pressure is connected to the tubing 11. The flush device 25 is operated in the flush mode to cause the whole system to fill with saline solution and to drive air out of the system. The button 50 of the flush device is released and the catheter is then inserted into the patient's blood vessel.

In this condition of normal operation, saline solution slowly drips into the patient's blood vessel in order to prevent clotting of the blood around the catheter 10. The saline solution in the tube 11 presents an essentially static column that conveys the patient's blood pressure to the transducer 26. Its fluctuations are monitored in real time by the monitor 27.

From time to time, it is desired to take a blood sample from the patient. To take the blood sample, the shunted stopcock 36 is turned to the position blocking the saline solution from pressurized bag 12 and opening the passage from the catheter 10 to the collection bag 35. The attendant then manipulates the flush device 25 to permit the blood pressure in the patient's cardiovascular system, nominally at 100 mmHg, to pump blood into the tubing 11. The introduction of blood into the tubing 11 drives saline solution into the bag 35, the bag 35 initially being at 0 mmHg. The pressure in the bag will never increase beyond about 30 mmHg and thus the patient always has the pressure to drive the saline into the bag.

The attendant observes the movement of blood in the catheter from the transparent tubing 11 until the blood has passed the sampling site 38. At that point, the flush passage is closed. The syringe 40 is applied to the sampling site to withdraw sufficient blood for the laboratory testing. That sampling operation having been completed, the attendant reverses the position of the shunted stopcock 36 so that the pressurized source of saline again is connected to the catheter. The attendant then opens the flush device to rapidly drive the patient's blood back into the patient's body. As soon as that is accomplished, the flush device is released and flow through the capillary tube is resumed.

In FIG. 3, there is shown an embodiment of the invention that prevents flow of air from the collection bag 35 to the stopcock 36 and, hence, the main line 11 to the patient. In accordance with this form of the invention, a duck bill valve 50 is connected between the third port 51 of the stopcock 36 and the collection bag 35. Any airtight connection of the duck bill valve to the system will be satisfactory. For example, each connection can be a spigot-in-socket connection which is sonic-welded or solvent-welded.

The duck bill valve per se consists of a two-part housing 52 having an elastomeric element 53 blocking passage through the valve. The elastomeric element is open at one end 54 by which the element is secured in the housing 52. At the other end 55, the element is normally closed by the resilience of the elastomeric material, the closure being on a line resembling a duck bill. When fluid under pressure enters the open end 54, it forces the closure line at 55 to part as shown in the broken lines 56. That creates a passage for the flow of fluid into the collection bag. Pressure on the other side of the duck bill element 53 will cause the lips at 55 to press more tightly against one another in order to completely block flow of air or any other fluid from the bag to the stopcock 36.

In an alternative form of the invention, an air elimination filter 60 is substituted for the duck bill valve 50. The filter 60 is a known element that permits passage of liquid through it but blocks passage of air through it. By interposing the filter 60 between the stopcock 36 and the collection bag 35, air is blocked from flowing to the line 11, but on the other hand, saline solution under pressure from the patient is permitted to flow through the filter 60 into the bag 35.

Figure 5:
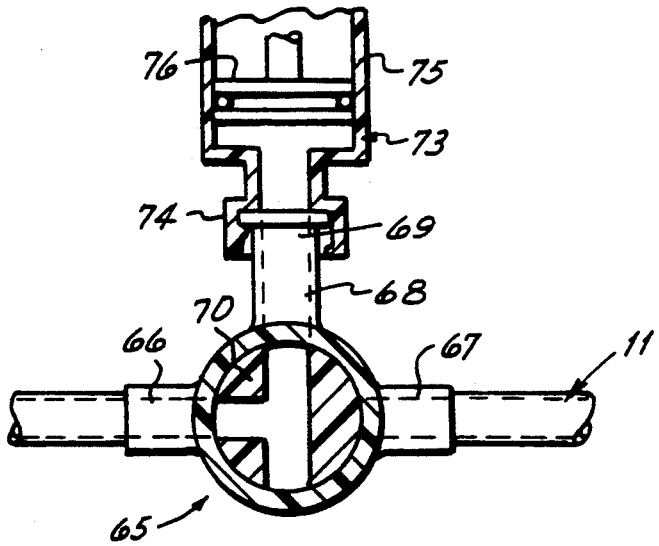
FIG. 5 is an enlarged cross-sectional view of an alternative form of the invention at the sampling site.

The alternative form of the sampling site is illustrated in FIG. 5. As shown in FIG. 5, a second stopcock 65 is placed in the line 11 as a substitute for the injection site 38 of FIG. 1. All other elements of the system remain the same. The stopcock has first and second ports 66 and 67 which connect it in series with the line 11. The stopcock has a third port 68 having a female Luer connector 69. The stopcock is an antishunt stopcock having a two-position plug 70. As shown, the plug 70 connects the port 66, which is connected to the catheter in the patient's blood vessel, to the third port 68. In this position, sampling at the third port is permitted. The second position simply provides a direct connection between ports 66 and 67 while the third port 68 is blocked.

A syringe 73 has a male Luer connector 74 by which the syringe can be attached to the third port 68 of the stopcock 65. The syringe has a barrel 75 and a plunger 76. By connecting the syringe to the third port 68 of the stopcock 65, and by opening the stopcock to the port 68, any blood that has been brought up to the sampling system, as described above, can be withdrawn into the syringe. After withdrawal, the port 68 is closed and the syringe is removed.

From the above disclosure of the general principles of the present invention and the preceding detailed description of a preferred embodiment, those skilled in the art will readily comprehend the various modifications to which the present invention is susceptible. Therefore, I desire to be limited only by the scope of the following claims and equivalents thereof:

I claim:

1. A blood sampling system comprising:
   a catheter for insertion into a patient's blood vessel,
   a source of saline solution,
   tubing connecting said source to said catheter,
   a stopcock in series with said tubing,
   a saline solution collection bag connected to said stopcock,
   said stopcock selectively connecting said catheter to said source or said catheter to said collection bag, and
   a sampling site in said tubing between said catheter and said stopcock.

2. A blood sampling system as in claim 1 further comprising:
   a one-way check valve connected between said bag and said stopcock and oriented to permit fluid flow only from said stop toward said bag.

3. A blood sampling system as in claim, 2 in which said check valve is a duck bill check valve.

4. A blood sampling system as in claim 1 further comprising:
   an air elimination filter connected between said bag and said stopcock to permit only fluid flow between said bag and stopcock, thereby blocking movement of air from said bag into said tubing connecting said source to said catheter.

5. A blood sampling system as in claim 1 in which said sampling site comprises:
   a second stopcock having three ports, first and second ports being connected in series in said tubing between said saline source and said catheter,
   and a third port having a fitting for a removable connection to a syringe,
   said stopcock providing, selectively, a connection between said saline source and said catheter and between said catheter and said third port,
   whereby a blood sample is taken by attaching a syringe to said third port, opening said first named stopcock between said catheter and said bag until blood passes said second stopcock, closing said first-named stopcock to said bag, opening said second stopcock to said third port, and drawing blood into said syringe.

* * * * *